(12) United States Patent
Sherwood

(10) Patent No.: US 8,174,818 B2
(45) Date of Patent: May 8, 2012

(54) METHOD FOR A CAPACITOR WITH A FLEXIBLE INTERCONNECT

(75) Inventor: Gregory J. Sherwood, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 333 days.

(21) Appl. No.: 12/642,582

(22) Filed: Dec. 18, 2009

(65) Prior Publication Data

US 2010/0095496 A1 Apr. 22, 2010

Related U.S. Application Data

(62) Division of application No. 11/124,989, filed on May 9, 2005, now Pat. No. 7,301,753.

(51) Int. Cl.
 *H01G 9/04* (2006.01)
(52) U.S. Cl. ........ 361/508; 361/503; 361/504; 361/509; 361/517; 361/519; 607/5; 607/7; 607/9
(58) Field of Classification Search .................. 361/508, 361/509, 503–504, 516–519; 607/5, 7, 9
See application file for complete search history.

(56) References Cited

U.S. PATENT DOCUMENTS

| | | |
|---|---|---|
| 3,182,238 A | 5/1965 | Toder et al. |
| 3,789,502 A | 2/1974 | Callins et al. |
| 4,136,435 A | 1/1979 | Li |
| 4,371,406 A | 2/1983 | Li |
| 4,425,412 A | 1/1984 | Dittmann et al. |
| 4,546,415 A | 10/1985 | Kent et al. |
| 4,571,662 A | 2/1986 | Conquest et al. |
| 4,614,194 A | 9/1986 | Jones et al. |
| 4,659,636 A | 4/1987 | Suzuki et al. |
| 4,683,516 A | 7/1987 | Miller |
| 4,843,518 A | 6/1989 | Okumura |
| 4,907,130 A | 3/1990 | Boulloy et al. |
| 4,987,519 A | 1/1991 | Hutchins et al. |
| 5,131,388 A | 7/1992 | Pless et al. |
| 5,195,019 A | 3/1993 | Hertz |
| 5,279,029 A | 1/1994 | Burns |
| 5,414,588 A | 5/1995 | Barbee, Jr. et al. |

(Continued)

FOREIGN PATENT DOCUMENTS

JP 52-004051 1/1977

(Continued)

OTHER PUBLICATIONS

"U.S. Appl. No. 11/124,989, Notice of Allowance mailed Jul. 16, 2007", 5 pgs.

(Continued)

*Primary Examiner* — Nguyen T Ha
(74) *Attorney, Agent, or Firm* — Schwegman, Lundberg & Woessner, P.A.

(57) ABSTRACT

The present subject matter includes a first capacitor stack including a first plurality of anode layers and a first plurality of cathode layers and a second capacitor stack including a second plurality of anode layers and a second plurality of cathode layers. In various embodiments, a flexible bus is welded to the first capacitor stack and to the second capacitor stack. The flexible bus is adapted to conduct electricity between the first capacitor stack and the second capacitor stack. Also, the present subject matter includes embodiments where the first capacitor stack and the second capacitor stack are disposed in a case filled with an electrolyte.

20 Claims, 5 Drawing Sheets

U.S. PATENT DOCUMENTS

| | | | |
|---|---|---|---|
| 5,422,200 A | 6/1995 | Hope et al. | |
| 5,493,471 A | 2/1996 | Walther et al. | |
| 5,500,534 A | 3/1996 | Robinson et al. | |
| 5,522,851 A | 6/1996 | Fayram | |
| 5,628,801 A | 5/1997 | MacFarlane et al. | |
| 5,660,737 A * | 8/1997 | Elias et al. | 216/6 |
| 5,667,909 A | 9/1997 | Rodriguez et al. | |
| 5,674,260 A | 10/1997 | Weinberg | |
| 5,688,698 A | 11/1997 | Robinson et al. | |
| 5,737,181 A | 4/1998 | Evans | |
| 5,754,394 A | 5/1998 | Evans et al. | |
| 5,776,628 A | 7/1998 | Kraft et al. | |
| 5,779,891 A | 7/1998 | Andelman | |
| 5,801,917 A | 9/1998 | Elias | |
| 5,855,995 A | 1/1999 | Haq et al. | |
| 5,867,363 A | 2/1999 | Tsai et al. | |
| 5,908,151 A | 6/1999 | Elias | |
| 5,922,215 A * | 7/1999 | Pless et al. | 216/6 |
| 5,930,109 A | 7/1999 | Fishler | |
| 5,963,418 A | 10/1999 | Greenwood, Jr. et al. | |
| 5,980,977 A | 11/1999 | Deng et al. | |
| 5,983,472 A | 11/1999 | Fayram et al. | |
| 6,004,692 A | 12/1999 | Muffoletto et al. | |
| 6,032,075 A | 2/2000 | Pignato et al. | |
| 6,094,788 A | 8/2000 | Farahmandi et al. | |
| 6,099,600 A | 8/2000 | Yan et al. | |
| 6,118,651 A | 9/2000 | Mehrotra et al. | |
| 6,139,986 A | 10/2000 | Kurokawa et al. | |
| 6,275,729 B1 | 8/2001 | O'Phelan et al. | |
| 6,388,866 B1 | 5/2002 | Rorvick et al. | |
| 6,402,793 B1 | 6/2002 | Miltich et al. | |
| 6,426,864 B1 * | 7/2002 | O'Phelan et al. | 361/509 |
| 6,442,015 B1 | 8/2002 | Niiori et al. | |
| 6,493,212 B1 | 12/2002 | Clarke et al. | |
| 6,498,951 B1 | 12/2002 | Larson et al. | |
| 6,509,588 B1 | 1/2003 | O'Phelan et al. | |
| 6,522,525 B1 | 2/2003 | O'Phelan et al. | |
| 6,556,863 B1 | 4/2003 | O'Phelan et al. | |
| 6,571,126 B1 | 5/2003 | O'Phelan et al. | |
| 6,699,265 B1 | 3/2004 | O'Phelan et al. | |
| 6,833,987 B1 | 12/2004 | O'Phelan | |
| 6,885,548 B2 | 4/2005 | Nyberg | |
| 6,890,363 B1 | 5/2005 | Sakai et al. | |
| 7,110,240 B2 | 9/2006 | Breyen et al. | |
| 7,154,739 B2 | 12/2006 | O'Phelan | |
| 7,180,727 B2 | 2/2007 | Poplett | |
| 7,196,899 B1 | 3/2007 | Feger et al. | |
| 7,301,753 B2 | 11/2007 | Sherwood | |
| 7,352,560 B2 | 4/2008 | Poplett et al. | |
| 7,532,456 B2 * | 5/2009 | Poplett | 361/508 |
| 7,656,646 B2 | 2/2010 | Sherwood | |
| 7,768,772 B2 * | 8/2010 | Doffing et al. | 361/520 |
| 2003/0077509 A1 | 4/2003 | Probst et al. | |
| 2004/0220627 A1 | 11/2004 | Crespi et al. | |
| 2006/0249774 A1 | 11/2006 | Sherwood | |
| 2007/0162077 A1 | 7/2007 | Sherwood | |
| 2008/0066278 A1 | 3/2008 | Sherwood | |

FOREIGN PATENT DOCUMENTS

| | | |
|---|---|---|
| JP | 59-083772 | 5/1984 |
| WO | WO-99/66985 A1 | 12/1999 |

OTHER PUBLICATIONS

"U.S. Appl. No. 11/124,989, Preliminary Amendment filed Dec. 20, 2005", 14 pgs.

"U.S. Appl. No. 11/124,989, Response filed Apr. 20, 2007 to Restriction Requirement mailed Mar. 22, 2007", 10 pgs.

"U.S. Appl. No. 11/124,989, Restriction Requirement mailed Mar. 22, 2007", 5 pgs.

"U.S. Appl. No. 11/943,299, Non-Final Office Action mailed Mar. 5, 2009", 6 pgs.

"U.S. Appl. No. 11/943,299, Notice of Allowance mailed Sep. 16, 2009", 8 Pgs.

"U.S. Appl. No. 11/943,299, Response filed Jun. 4, 2009 to Non Final Office Action mailed Mar. 5, 2009", 10 pgs.

Dombro, R., "Method and Apparatus for Insulative Film for Capacitor Components", U.S. Appl. No. 11/124,792, filed May 9, 2005, 44 pgs.

Poplett, J. M., "Method and Apparatus for Interconnecting Electrodes With Partial Titanium Coating", U.S. Appl. No. 11/124,706, filed May 9, 2005, 46 pgs.

Sherwood, G. J., "Method and Apparatus for High Voltage Aluminum Capacitor Design", U.S. Appl. No. 11/182,707, filed Jul. 15, 2005, 239 pgs.

Sherwood, G. J, "Method and Apparatus for Providing Flexible Partially Etched Capacitor Electrode Interconnect", U.S. Appl. No. 60/588,905, filed Jul. 16, 2004, 241 pgs.

* cited by examiner

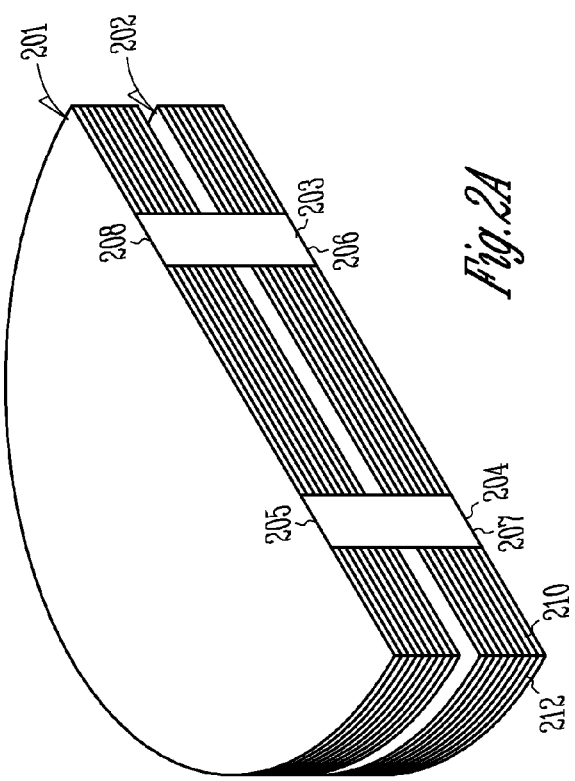
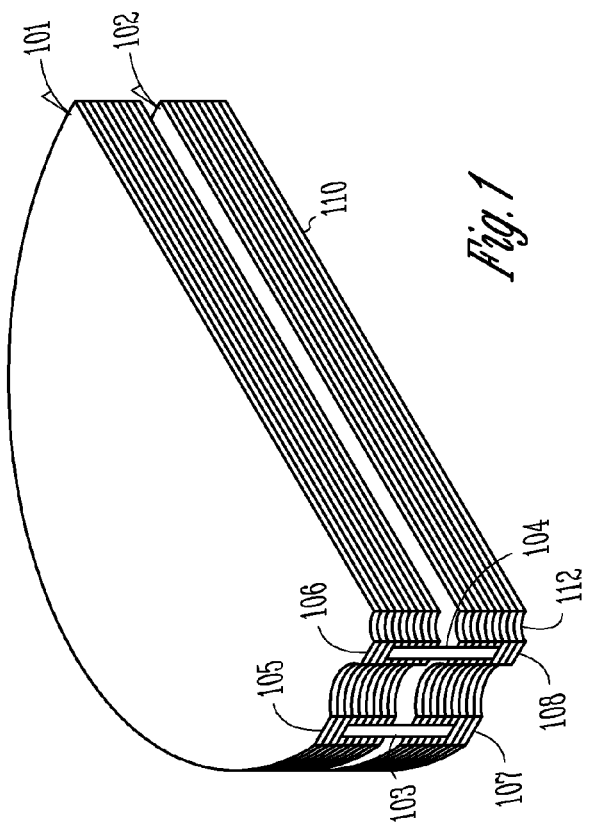

METHOD FOR A CAPACITOR WITH A FLEXIBLE INTERCONNECT

CROSS REFERENCE TO RELATED APPLICATIONS

The present application is a divisional of U.S. patent application "Method and apparatus for a capacitor with flexible bus" to Sherwood, Ser. No. 11/124,989 (hereinafter the '989 patent), filed May 9, 2005, now U.S. Pat. No. 7,301,753, and claims the benefit of priority to that case through related U.S. patent application "Method and apparatus for a capacitor with flexible interconnect" to Sherwood, Ser. No. 11/943,299, filed Nov. 20, 2007, which is a still-pending continuation of the '989 patent, each of which are incorporated herein by reference in their entirety.

The present application is related to the following commonly assigned U.S. Patents which are incorporated by reference in their entirety: "High-Energy Capacitors for Implantable Defibrillators" to O'Phelan, et al., U.S. Pat. No. 6,556,863, filed Oct. 2, 1998, issued Apr. 29, 2003; "Flat Capacitor for an Implantable Medical Device" to O'Phelan, et al., U.S. Pat. No. 6,699,265, filed Nov. 3, 2000, issued Mar. 2, 2004. Additionally, the present application is related to the following Provisional U.S. patent application which is assigned to the same assignee and is incorporated by reference in its entirety: "Method and Apparatus for Single High Voltage Aluminum Capacitor Design," Ser. No. 60/588,905, filed on Jul. 16, 2004. The present application is related to the following commonly assigned U.S. patent applications which are incorporated by reference in their entirety: "Method and Apparatus for Interconnection Cathodes with Partial Titanium Coating" to Poplett, et al., Ser. No. 11/124,706, filed on May 9, 2005, now U.S. Pat. No. 7,352,560; "Method and Apparatus for Insulative Film on Capacitor Components" to Dombro, et al., Ser. No. 11/124,792, filed on May 9, 2005, now U.S. Pat. No. 7,426,104.

TECHNICAL FIELD

This disclosure relates generally to capacitors, and more particularly to a capacitor with one or more flexible bus connections.

BACKGROUND

There is an ever-increasing interest in making electronic devices physically smaller. Consequently, electrical components become more compact as technologies are improved. However, such advances in technology also bring about additional problems. One such problem involves interconnects between various components and interconnects within components.

Interconnects are especially problematic with devices incorporating multiple layers. One such component is the capacitor. Capacitors provide improved charge storage and energy density using multiple conductive layers and advanced dielectrics. As the layers become more complex and smaller in dimensions, problems arise with interconnections.

Thus, there is a need in the art for improved technologies for interconnects between layered devices. The systems used to interconnect the multiple layers should be readily adapted for manufacturing. The interconnects should form robust connections without damaging the multiple layers and without sacrificing substantial performance of the component. Connections should accommodate varying capacitor component configurations.

SUMMARY

The above-mentioned problems and others not expressly discussed herein are addressed by the present subject matter and will be understood by reading and studying this specification.

One embodiment of the present subject matter includes an apparatus, comprising a first capacitor stack with a first plurality of anode layers and a first plurality of cathode layers, with a second capacitor stack including a second plurality of anode layers and a second plurality of cathode layers. Connecting the first capacitor stack and the second capacitor stack is a flexible connection adapted to permit rotation of the first capacitor stack with respect to the second capacitor stack and into a splayed position. The embodiment also includes a case with material defining a first aperture, the first aperture sized for passage of the first capacitor stack, the second capacitor stack, and the flexible bus, and a lid conforming to the first aperture and sealably connected to the first aperture. The first capacitor stack, the second capacitor stack, and the flexible bus are disposed in the case, and electrolyte is disposed in the case.

Another embodiment of the present subject matter includes a method of forming a first capacitor stack from at least one element and forming a second capacitor from at least one element, and stacking the first capacitor stack onto the second capacitor stack, the first capacitor stack and second capacitor stack defining a welding position. This embodiment includes welding a flexible bus to the first capacitor stack and the second capacitor stack while the first capacitor stack and second capacitor stack are in the welding position, rotating the second capacitor stack away from the first capacitor stack and into a splayed position, and positioning the first capacitor stack and the second capacitor stack in a case in the splayed position and filling the case with electrolyte.

One embodiment of the present subject matter includes an apparatus comprising a first capacitor stack including a first plurality of anode layers and a first plurality of cathode layers, a second capacitor stack including a second plurality of anode layers and a second plurality of cathode layers, and means for connecting the first capacitor stack and the second capacitor stack, the means adapted to permit rotation of the first capacitor stack relative to the second capacitor stack. The embodiment includes a case including material defining a first aperture, the first aperture sized for passage of the first capacitor stack, the second capacitor stack, and the flexible bus, and a lid conforming to the first aperture and sealably connected to the first aperture, as well as electrolyte disposed in the case.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

FIG. 1 is a perspective view of coupled capacitor electrode stacks, according to one embodiment of the present subject matter;

FIG. 2A is a perspective view of coupled capacitor electrode stacks, according to one embodiment of the present subject matter;

DETAILED DESCRIPTION

Figure 2B:
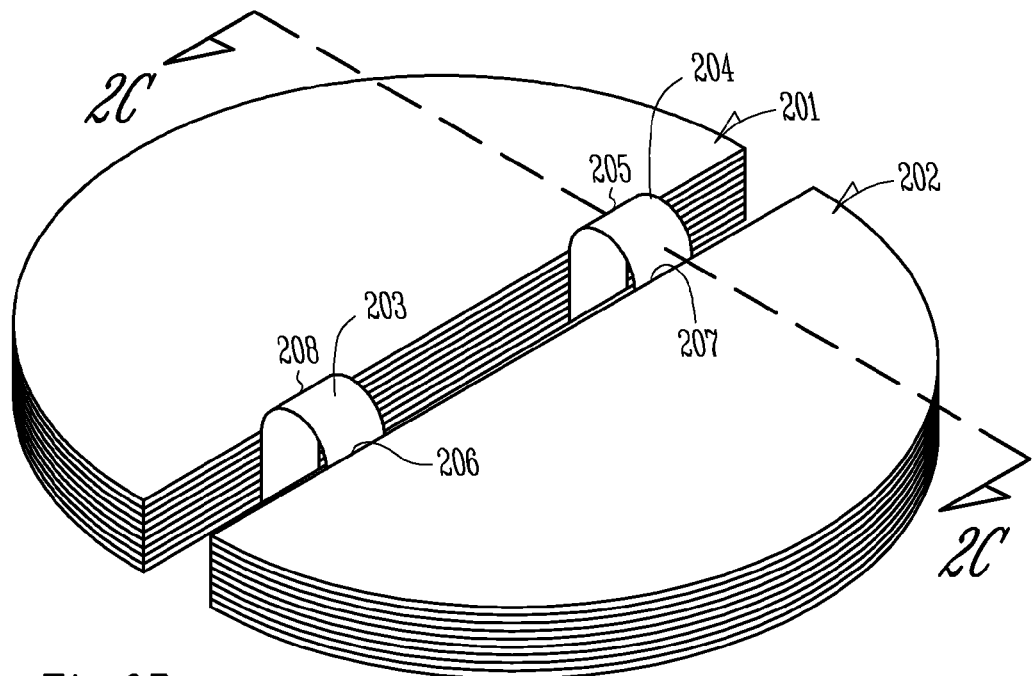
FIG. 2B is a perspective view of coupled capacitor electrode stacks in a splayed position, according to one embodiment of the present subject matter.

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references may contemplate more than one embodiment. The following detailed description is, therefore, not to be taken in a limiting sense, and the scope is defined only by the appended claims, along with the full scope of legal equivalents to which such claims are entitled.

FIG. 1 is a perspective view of coupled capacitor electrode stacks, according to one embodiment of the present subject matter. The capacitor electrode stack includes alternating anode and cathode layers separated by separator paper in various embodiments, but other embodiments are within the scope of the present subject matter. Various embodiments include from 16 substantially planar cathode layers to 20 substantially planar cathode layers, and from 52 substantially planar anode layers to 60 substantially planar anode layers. One embodiment includes 18 substantially planar cathode layers, and 58 substantially planar anode layers. Various embodiments include anode layers positioned adjacent to one another without isolation from each other, by, for example, separator papers.

In some examples, each anode layers is approximately 0.004 inches thick. Additionally, in various examples, each cathode layers is approximately 0.001 inches thick. Further, various examples include a separator which is between approximately 0.00045 and 0.00055 inches thick. In one example, the anodes are isolated from the cathodes by two sheets of approximately 0.0005 inch thick separator paper.

One method of adjusting the thickness of an electrode stack configured as such is by adding or subtracting electrode layers or separator papers. Varying numbers of anodes, cathodes and separators can account not only for a selective electrode stack thickness, but also for selecting a balance between the electric field strength of the whole anode and the electrode field strength of the whole cathode.

Various embodiments within the scope of the present subject matter result in capacitor stacks of various sizes and shapes. For example, in one embodiment, a combination of a first capacitor stack and a second capacitor stack has a mass of between approximately 10.2 grams and 11.1 grams. Various capacitor embodiments include additional components, such as a case, and have additional mass. Although the illustration demonstrates an example in which electrode stack 101 and electrode stack 102 are D-shaped, in varying embodiments, the they do not have matching shapes. Possible shapes include, but are not limited to, rectangular shapes, circular shapes, oval shapes, square shapes, or other symmetrical or asymmetrical shapes. In the example illustration, the stack includes a short sidewall 112 and a long sidewall 110.

Various embodiments include a coupled first and second capacitor stack. In one embodiment, the first capacitor stack is adapted to deliver between 7.0 Joules/cubic centimeter and 8.5 Joules/cubic centimeter. Some embodiments are adapted to deliver about 7.7 Joules/cubic centimeter. In some embodiments, the anode has a capacitance of between approximately 0.70 and 0.85 microfarads per square centimeter when charged at approximately 550 volts. In various embodiments, these ranges are available at a voltage of between about 410 volts to about 610 volts. An example capacitor suitable for use with the present subject matter is included in related application "Method and Apparatus for Single High Voltage Aluminum Capacitor Design," Ser. No. 60/588,905, filed on Jul. 16, 2004, at or around pages 12-37, 39, 41-140, incorporated herein by reference, but not by way of limitation.

In various embodiments, the one or more stacks are disposed in a case, and linked with other components, a state which affects some of these values. For example, in one packaged embodiment, including a case and terminals, the energy density available ranges from about 5.3 joules per cubic centimeter of capacitor stack volume to about 6.3 joules per cubic centimeter of capacitor stack volume. Some embodiments are adapted to deliver about 5.8 joules. In various embodiments, these ranges are available at a voltage of between about 410 volts to about 610 volts.

The energy storing capacity of the present subject matter is due, in part, to anode foils which include an aluminum substrate at least partially encased in a dielectric. Various dielectrics include metallic oxide layers such as aluminum oxide ($Al_2O_3$). In various embodiments, dielectric layers have a thickness sufficient to withstand approximately 441 volts or greater. In one embodiment, layers have a thickness sufficient to withstand up to 600 volts. Other embodiments withstand 600 volts to 800 volts or greater. In various embodiments, the anode layers have a dielectric thickness sufficient to withstand approximately 455 volts to approximately 575 volts during operation. In some embodiments, anode layers have a dielectric thickness sufficient to withstand between about 490 volts and about 540 volts during operation. Other embodiments withstand from about 500 volts to about 530 volts during operation. One embodiment is able to withstand about 515 volts during operation.

In various embodiments, dielectric layers on anodes have a thickness conforming to and covering the etched surface to a height of from about 455 nanometers to about 575 nanometers. Additional embodiments include dielectric layers ranging from about 573 nm to about 1200 nm. In some embodiments, the dielectric layer ranges from about 490 nanometers to about 540 nanometers. Other embodiments range between about 500 nanometers and about 530 nanometers. One embodiment includes approximately 515 nm. An additional embodiment has a thickness conforming to and covering the substrate to a height of at least 540 nm. It should be noted that due to the nature of the formation of a dielectric surface variations in thickness can manifest.

In various embodiments, a cathode comprises one or more interconnected foils. In some embodiments, a cathode can include aluminum, tantalum, hafnium, niobium, titanium, zirconium, and combinations of these metals. In one embodiment, cathode is constructed by coating an aluminum (98% purity or higher) base metal with titanium oxide, titanium nitride, or titanium pentoxide using sputtering, plating, vacuum deposition, or other coating techniques. In some embodiments, titanium itself is used with a subsequent processing step to oxidize the titanium resulting in $TiO$, $TiO_2$, $TiN$, $Ti_2O_5$, or other high dielectric constant oxide. Various coatings are present in thicknesses ranging from about 200 nanometers to about 1000 nanometers. One example includes a coating of about 500 nanometers in thickness.

The resulting titanium coated cathode material has a higher capacitance per unit area than traditional aluminum electrolytic capacitor cathodes. Traditional cathodes which are 98% aluminum purity or higher generally have capacitance per unit area of approximately 250 uF/cm$^2$ for 30 micron thick foil, with an oxide breakdown voltage in the 1-3 volt range. However, a cathode as described above results in a capacitance per unit area which, in some embodiments, is as high as 1000 uF/cm$^2$ or more.

In various embodiments, the present subject matter provides a cathode foil which can be paired with several layers of anodic foil without exceeding the oxide breakdown voltage. When using a traditional cathode to service several layers (2 or more) of anodic foil, the cathode voltage may rise as high as 5 or more volts, which is usually greater than the breakdown voltage. When this occurs, the aluminum cathode begins to form oxide by a hydration process which extracts oxygen from the water present in the electrolyte. The reaction produces hydrogen as a byproduct which in turn has the effect of creating an internal pressure within the capacitor causing an undesirable mechanical bulge in the layers from the capacitor stack, or in the case. Therefore, in some embodiments, the titanium coated cathode described above serves as a corrective mechanism for hydrogen gas generation.

Stacked layers will move with respect to one another unless they are constrained. In various embodiments, one or more of the coupled capacitor stacks are bound. The capacitor stacks can be bound using varying methods. For example, one embodiment includes capacitor stacks bound with adhesive polymeric tape. An additional embodiment includes capacitor stacks bound with a heat-shrinkable polymeric film. Various combinations of these embodiments are possible as well. One embodiment uses a single polymeric film to bind a plurality of capacitor stacks. Additional embodiments include binding apparatus and methods not enumerated here. Generally, bound embodiments retain the capacitor electrodes in a stack form. In some embodiments, binding apparatus, such as shrink wrap conformable with heat, are electrically insulative, effecting a dielectric boundary between the capacitor stacks and/or the capacitor case. Additional embodiments allow electrolyte to flow around the binding structure and into the capacitor stack. Various embodiments featuring a heat-shrinkable wrap use methods and structures disclosed in related U.S. patent application "Method and Apparatus for Insulative Film on Capacitor Components" to Dombro, et al., Ser. No. 11/124,792, filed on May 9, 2005, the contents of which are incorporated herein by reference, but not by way of limitation.

In varying embodiments, a first flexible bus 103 and a second flexible bus 104 connect capacitor stack 101 to capacitor stack 102. In some of these embodiments, the first flexible bus 103 and second flexible bus 104 serve to connect the stacks mechanically. In various embodiments, first flexible bus 103 and a second flexible bus 104 are metallic, and are welded to portions of the electrode stacks. In some embodiments, connection occurs at a portion of an electrode at which dielectric or other coating is substantially absent. In some of these embodiments, a mask is used to limit the presence of a coating. In various embodiments, applying a mask to an electrode layer includes application of a mask as is discussed in related application "Method and Apparatus for Single High Voltage Aluminum Capacitor Design," Ser. No. 60/588,905, filed on Jul. 16, 2004 on or around pages 32-34, the teachings of which are incorporated herein by reference, but not by way of limitation. Additional embodiments remove a coating, as is discussed in related application "Method and Apparatus for Interconnection Cathodes with Partial Titanium Coating" to Poplett, et al., Ser. No. 11/124,706, filed on May 9, 2005 at or around pages 8-25, which are incorporated herein by reference, but not by way of limitation.

In one example, electrode stack 101 includes a surface 105 adapted for connection to a flexible bus. In some embodiments, the surface is substantially planar, and is suited for welding. Additionally, in some embodiments, the surface is formed by a plurality of abutting edges of individual layers. In one example, the surface is comprised of a series of metallic layers welded together with an edge-welding process which uses a laser, such as a Lumonics JK702 Nd-YAG laser welder using settings of approximately 1.4 Joules at a frequency of 100 hertz. In this example, the laser power at approximately 110 watts, with a pulse height of approximately 22%, and a pulse width of approximately 1.4 milliseconds.

Connection surfaces, such as surface 105, are useful in a variety of applications. Providing a surface 105 and/or a surface 106 enables economical attachment of a flexible bus, in varying embodiments. For example, in one embodiment, the flexible bus 103 is a metallic strip soldered to surface 105. Additional methods and structure for connecting the flexible bus to the surface 105 fall within the scope of the present subject matter. In one example, the flexible bus is laser welded to the surface. In additional embodiments, solid-state welding is used.

In varying embodiments, laser welding the flexible bus 103 and/or 104 to a surface 105 and/or 106 requires a surface 105 which can withstand laser welding. In some embodiments, this is achieved by edge-welding two ore more electrode layers together.

In varying embodiments, the electrode stacks are connected electrically. In some of these embodiments, the flexible bus 103 and/or 104 is conductive. For example, electrode stack 101 includes surface 105 which, in various embodiments, is an anodic connection surface. In varying embodiments, two or more layers of anode are coupled and define surface 105. Additionally, electrode stack 102 includes surface 107, which is an anodic connection surface. In embodiment where flexible bus 103 is in electrical communication with surface 105 and surface 107, the anodes of capacitor stack 101 and 102 are connected in parallel. In additional embodiments, cathodic surface 106 and cathodic surface 108 are in electrical communication through flexible bus 104.

FIG. 2A is a perspective view of coupled capacitor electrode stacks, according to one embodiment of the present subject matter. In varying embodiments, the capacitor electrode stacks are elongate, and hinged along a long sidewall 210, but in additional embodiments, they are hinged along a short sidewall 212. In varying embodiments, the device includes electrode stacks 201 and 202, flexible buses 203 and 204, and electrode surfaces for attachment of a flexible bus 207 and 208.

FIG. 2B demonstrates a first capacitor stack and a second capacitor stack in physical isolation. In various embodiments, electrode stack 201 is semi-circular shaped, and electrode stack 202 is semi-circular shaped. Flexible bus 204 connects to electrode stack 201 at surface 205, and additionally connects to electrode stack 202 at surface 207, in some embodiments. Additionally, flexible bus 203 connects to electrode stack 201 at surface 208, and further connects to electrode stack 202 at surface 206.

Flexible buses 204 and/or 203, in varying embodiments, comprise a thin aluminum strip. Depending on the material used, the flexible buses are capable of a single deformation, or multiple deformations. In some embodiments, the flexible buses comprise additional materials, such as tantalum or titanium.

The combined system is suited to orient electrode stack 201 in a movable fashion with respect to electrode stack 202, such movement constrained by one or more flexible buses. In the example illustrated, the electrode stacks are oriented so that two semi-circular electrode stacks, which were stacked unto one another in one state, are placed in an adjacent, coplanar fashion in a splayed state. Although the example in a splayed position presents electrode stacks 201 and 202 in a flat arrangement, other arrangements are within the scope of the present subject matter, including arrangements where the stacks are at various angles, including acute and obtuse angles, and orthogonal arrangements.

Figure 2C:
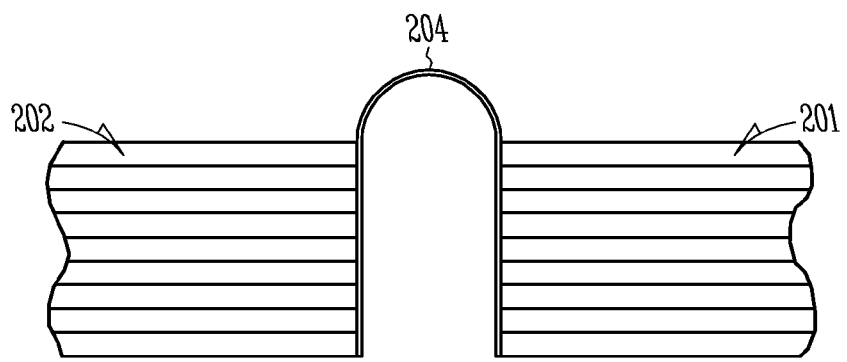
FIG. 2C is a side view of a cross section from FIG. 2B, the cross section taken at the line labeled "2C" in FIG. 2B, according to one embodiment of the present subject matter.

FIG. 2C is a side view of a cross section from FIG. 2B, the cross section taken at the line labeled "2C" in FIG. 2B, according to one embodiment of the present subject matter. The coplanar state of electrode stack 202 and electrode stack 201 is illustrated. Additionally, flexible bus 204 is illustrated.

By enabling movement of one electrode stack with respect to another, varying benefits are realized. For example, manufacturing is simplified. In one example, placing one or more capacitor interconnects along a common geometric plane, as is demonstrated in example FIG. 2A, enables welding along a bus with a welding process which moves along two axes. Two axis processes are simpler than three axis processes. As such, in varying embodiments, the cycle time for the welding process can be decreased. In some examples, a weld performed while traversing a single axis is sufficient, further simplifying manufacturing. An additional benefit includes improved packaging. The electrode stack in FIG. 2C, for example, is approximately half as thick as the electrode stack of FIG. 2A.

Figure 3A:
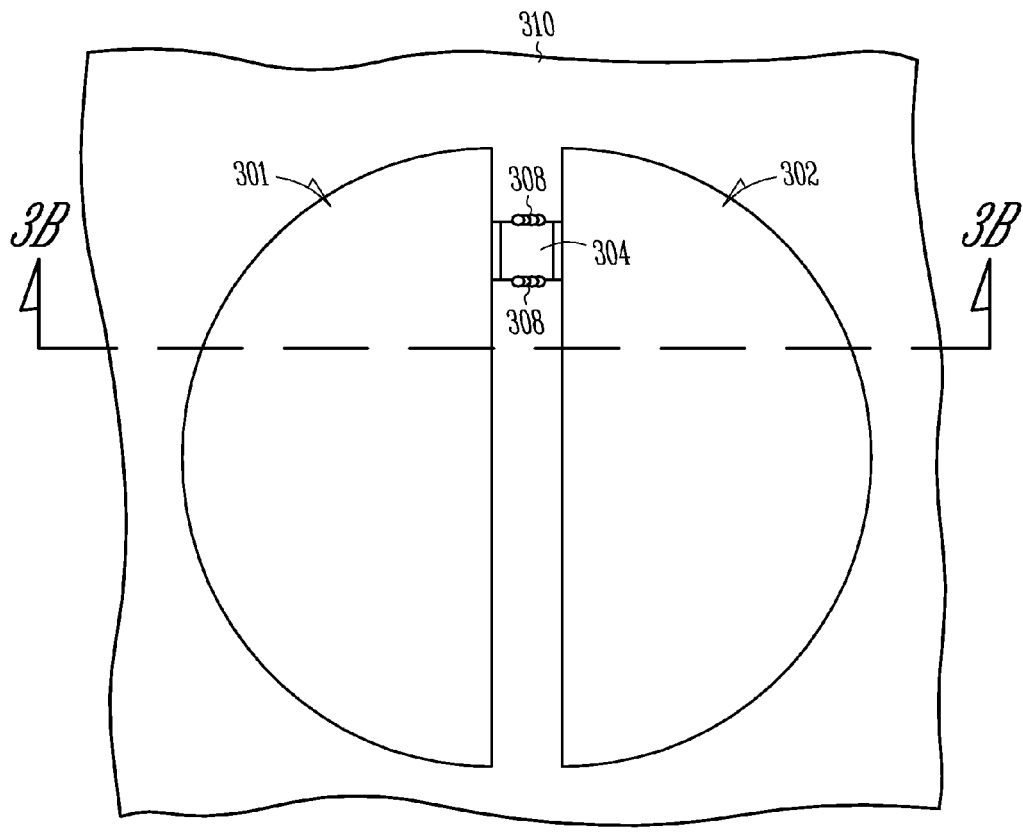
FIG. 3A is a top view of coupled capacitor electrode stacks welded to a plate, according to one embodiment of the present subject matter.

In various embodiments, the present subject matter provides a novel connection to external components, as well. FIG. 3A is a top view of coupled capacitor stacks welded to a plate, according to one embodiment of the present subject matter. In varying embodiments, the plate 310 is adapted for welding, and a flexible bus 304 is welded to the plate 310. The weld connection, in varying embodiments, includes welds 308. The flexible bus 304 is connected to electrode stack 301 and electrode stack 302.

The weld connection 308 is created in varying ways. For example, the flexible bus 304 includes an arc (a fold) which has an apex. When this apex is placed along the plate, it touches the plate along an axis of intersection. This axis of intersection, in varying embodiments, terminates at the edges of the flexible bus 304. At these terminations, weld energy can be directed.

Through using the methods and materials discussed herein, an improved capacitor connection to external components is realized. For example, in one embodiment, the flexible bus is connected to a cathodic surface of electrode stack 301, and is further connected to a cathodic surface of electrode stack 302. Additionally, plate 310 is part of a cathodic capacitor case. By connecting the electrode stacks to the cathodic case as such, capacitors with fewer components are constructed.

In varying examples, the weld(s) 308 are created by directing a laser into a weld target. However, other manners of directing energy at the weld target are within the scope of the present subject matter, including solid-state welding.

Figure 3B:
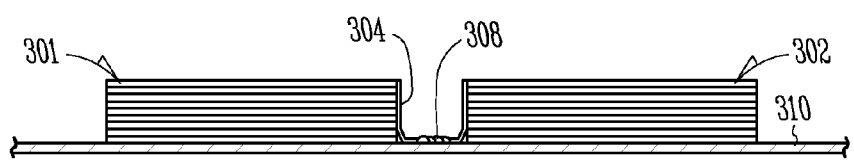
FIG. 3B is a side view of a cross section taken from FIG. 3A at the line labeled "3B", according to one embodiment of the present subject matter.

FIG. 3B is a side view of a cross section taken from FIG. 3A at the line labeled "3B," according to one embodiment of the present subject matter. In varying embodiments, the view provides alternate detail of flexible bus 304, and its connection to electrode stack 301, electrode stack 302, and its welded connection 308 to plate 310.

Figure 4:
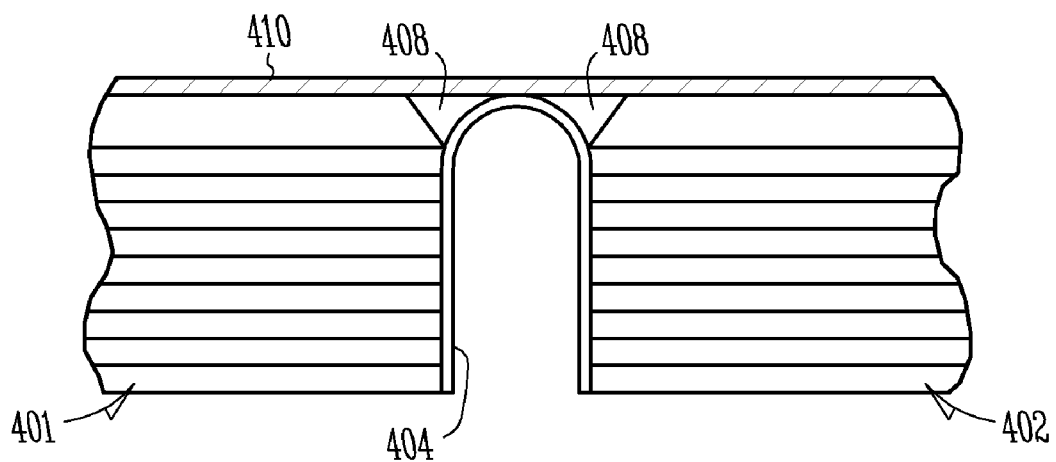
FIG. 4 is a side view of a cross section of coupled capacitor stacks showing a coupling welded to a plate, according to one embodiment of the present subject matter.

FIG. 4 is a side view of a cross section of coupled capacitor stacks showing a coupling welded to a plate, according to one embodiment of the present subject matter. In varying embodiments, the illustration includes a plate 410 welded 408 to flexible bus 404. Additionally, the flexible bus 404 is connected to electrode stack 401 and electrode stack 402, in varying examples. The view shows an alternate method of welding. The welds 408 are formed by welding parallel to the axis defined by contact between the plate 410 and the flexible bus 404.

The present subject matter provided multiple benefits in application. One example use includes a first capacitor stack including a first plurality of anode layers and a first plurality of cathode layers, and a second capacitor stack including a second plurality of anode layers and a second plurality of cathode layers, with a flexible bus welded to the first capacitor stack and to the second capacitor stack, the flexible bus adapted to conduct electricity between the first capacitor stack and the second capacitor stack. In various embodiments, the capacitor has a case, the case having a first opening sized for passage of the connected first capacitor stack and second capacitor stack. The interconnected first capacitors stack and second capacitor stack, in various embodiments, are disposed in the case through the first opening. Some embodiments include a case which is metallic and conductive. In various embodiments, the case is between approximately 0.010 and 0.012 inches thick and is an aluminum alloy. Also, in some embodiments, the cathode of the connected first capacitor stack and second capacitor stack is connected to the case.

In various embodiments, a lid is sealably connected to the first opening. Additionally, the case has a fill-port opening, and a feedthrough opening, in various embodiments. The feedthrough opening is a sealed opening through which one or more conductors pass, according to various embodiments. In embodiments where the cathode is connected to the case, an anode conductor, connected to the anode of the interconnected first capacitor stack and second capacitor stack, passes through the feedthrough opening. The feedthrough opening is sealable, in various examples, and the anode conductor extends to other electronics, in various embodiments. Additionally, in some embodiments, a cathode conductor is connected to the case, and extends to other electronics.

It should be noted that the present subject matter includes connecting the capacitor to various components. For example, in various embodiments the capacitor is inserted into an implantable medical device suited for delivering electrical stimulation to a patient. In one embodiment, the method of the present subject matter includes installing a capacitor in an implantable cardioverter defibrillator which is adapted for implant in a patient, and which is also adapted to deliver high voltage pulses to a patient in order to promote cardiac wellness. For example, in various embodiments, one method of the present subject matter includes providing a defibrillator case having circuitry disposed in the case.

Additionally, various embodiments include implanting an implantable cardioverter defibrillator in a patient. Also, some examples include connecting the cardiac system of a patient to the implantable cardioverter defibrillator. In one example, circuitry in the capacitor controls the discharge of electrical energy from the capacitor to the patient. Overall, in various embodiments, the method of the present subject matter enables improved delivery of electrical stimulation to a patient using an implantable cardioverter defibrillator.

One of ordinary skill in the art will understand that the modules and other circuitry shown and described herein are implemented using software, hardware, and combinations of software and hardware. As such, the term circuitry is intended to encompass software implementations, hardware implementations, and software and hardware implementations.

The methods illustrated in this disclosure are not intended to be exclusive of methods within the scope of the present subject matter. Those of ordinary skill in the art will understand, upon reading and comprehending this disclosure, other method configurations are within the scope of the present subject matter. The identified embodiments, and portions of the illustrated embodiments, are not necessarily mutually exclusive. These embodiments, or portions thereof, are combined in various embodiments. For example, various embodiments combine two or more of the demonstrated processes.

Figure 5:
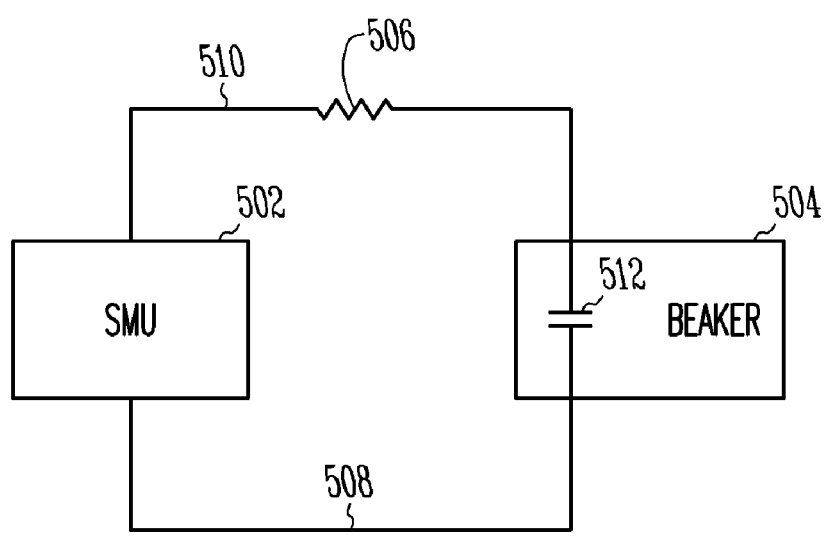
FIG. 5 is a schematic of a process for aging a capacitor, according to one embodiment of the present subject matter.

FIG. 5 illustrates a schematic for an experiment, according to one embodiment of the present subject matter. In an example experiment, a ribbon shaped flexible bus of approximately 0.15 inches is used to connect two electrode stacks at a cathode surface, and another ribbon shaped flexible bus of approximately 0.15 inches is used to connect the two electrode stacks at an anode surface. The combined system 512 is then aged, as is known in the art. For example, the capacitor is placed in a beaker 504 of solution. In various embodiments, the beaker contains an ethylene glycol based electrolyte adapted for use with a range of test voltages, such as voltages ranging from 50 volts to 400 volts.

In various embodiments, the capacitor is connected to a system measurement unit (SMU) 502, which acts, in part, as a power source. An example system measurement unit is available from KEITHLEY INSTRUMENTS, INC. Additionally, the experiment uses a 20 kilo-ohm resistor 506 to increase the rate of discharge, but in additional embodiments, a 40 kilo-ohm resistor is used. The system is connected by conductors 510 and 508.

The aging occurred first at 60 degrees Celsius with an applied voltage of between approximately 50 volts to approximately 350 volts. The capacitor is aged until the leakage current falls below 200 microamperes. This can takes about 100 minutes. Further aging then occurred at 40 degrees Celsius, with an applied voltage of between about 350 volts to about 397.5 volts, until the leakage current falls below about 250 micro amperes.

In the experiment, an individual capacitor stack, for example, stack 101 or stack 102 pictured in illustration FIG. 1, recorded from about 15.17 joules of energy delivered during a test to about 15.23 joules of energy delivered, but when connected in parallel, the coupled design recorded from about 31.39 joules delivered to about 31.55 joules, which represented more than double the joules of the single capacitor embodiment. Due to the internal efficiencies of the capacitor, the parallel connection is useful for enabling this improved energy delivery. This can be due to decreases in equivalent series resistance of the capacitors.

Figure 6:
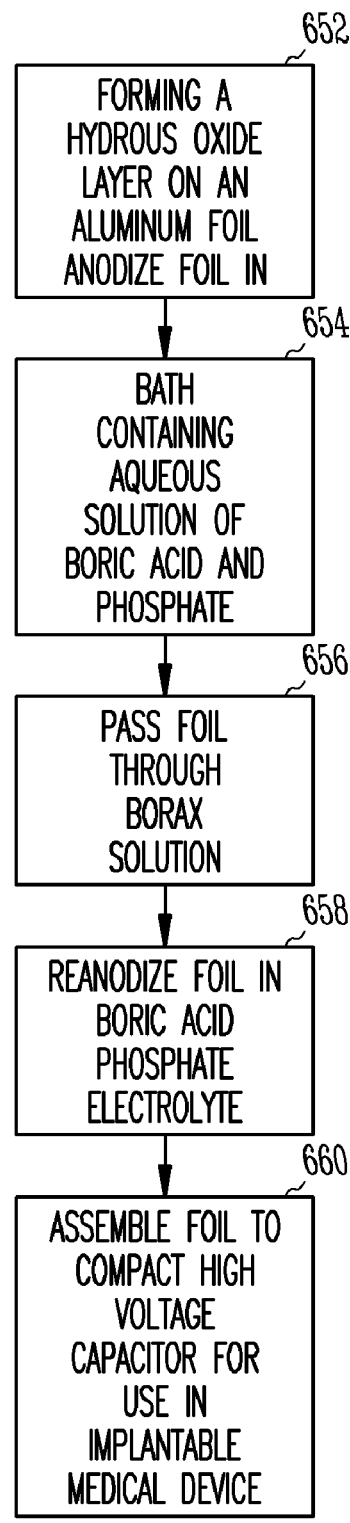
FIG. 6 is a flow diagram of a process for producing an anode, according to one embodiment of the present subject matter.

FIG. 6 illustrates an example process for the anodization of aluminum electrolytic capacitor foil, according to the present subject matter. In varying embodiments, the present subject matter is capable of producing anodized aluminum electrolytic capacitor foil at a formation voltage from about 200 volts to about 760 volts, which can result in a capacitor with a working voltage from about 150 volts to about 570 volts. For example, the present subject matter encompasses aluminum oxide formed at between approximately 600 volts and approximately 760 volts. Additionally, the present subject matter encompasses embodiments where anodization occurs from about 653 volts to about 720 volts. Additionally, the present subject matter encompasses embodiments wherein anodization occurs from about 667 volts to about 707 volts during formation.

Varied processes can be utilized to produce the aluminum foil of the present subject matter. For example, one process includes forming a hydrous oxide layer on an aluminum foil by immersing the foil in boiling deionized water 652. The aluminum foil is also subjected to electrochemical anodization in a bath containing an anodizing electrolyte 654 composed of an aqueous solution of boric acid, a phosphate, and a reagent. Additionally, the anodizing electrolyte contains a phosphate. In various embodiments, the anodizing electrolyte is at a pH of approximately 4.0 to approximately 6.0. In some examples, the foil is passed through a bath containing a borax solution 656. Borax, in various embodiments, includes a hydrated sodium borate, $Na_2B_4O_7.10H_2O$, and is an ore of boron.

In varying embodiments, the foil is reanodized in the boric acid-phosphate electrolyte previously discussed 658. In various embodiments of the present subject matter, the process produces a stabilized foil suitable for oxide formation of up to approximately 760 volts.

In various embodiments, the anodizing electrolyte used in block 654 and 656 contains about 10 grams per liter to about 120 grams per liter of boric acid and approximately 2 to approximately 50 parts per million phosphate, preferably as phosphoric acid, and sufficient alkaline reagent to lower the resistivity to within approximately 1500 ohm-cm to approximately 3600 ohm-cm and increase the pH from about 4.0 to about 6.0 for best anodization efficiency and foil quality.

In some embodiments, the borax bath contains 0.001 to 0.05 moles/liter of borax. Because the anodizing electrolyte is acidic, in various embodiments, the borax bath is buffered with sodium carbonate to prevent lowering of the pH by dragout of the acidic electrolyte. Additionally, in various embodiments, the borax bath is buffered to lower its resistivity. In one example, the pH of the bath is from about 8.5 to about 9.5, and the temperature is at least approximately 80 degrees Celsius. In varying embodiments, the sodium concentration is approximately 0.005 to approximately 0.05M, preferably about 0.02 M. It should be noted that concentrations of less than approximately 0.005M are too dilute to control properly, and concentrations above approximately 0.05M increase the pH, resulting in a more reactive solution which degrades barrier layer oxide quality.

In varying embodiments of the present subject matter, the presence of at least approximately 2 parts per million phosphate in the acidic anodizing electrolyte is critical. For example, this presence initiates stabilization of the foil so that solely hydrous oxide dissolves in the alkaline borax bath, without damage to the barrier layer dielectric oxide. In varying embodiments, this lowers ESR (equivalent series resistance) of the anodized foil.

Additionally, in various embodiments, when the foil is reanodized following the alkaline borax bath, the foil surface is alkaline and reacts electrochemically with the phosphate, which, in various embodiments, results in the incorporation of phosphate into the dielectric oxide. In varying examples, the alkaline foil surface includes an alkaline metal aluminate, and in one embodiment includes a sodium aluminate. It should be noted that the amount of allowable phosphate in the anodizing electrolyte, in various embodiments, is inversely proportional to the voltage at which the foil is being anodized. For example, in one embodiment, using greater than approximately 24 parts per million results in failure during oxide formation at around 650 volts. In embodiments where approximately 50 parts per million of phosphate is exceeded, the electrolyte scintillates at the foil interface, resulting in damaged, unstable foil. One benefit of the present subject matter is that an electrode is produced which can tolerate a high formation voltage without scintillation at the boundary layer of the foil. It should be noted that anodization temperature should be maintained from about 85 degrees Celsius to about 95 degrees Celsius, as variance outside of these values results in a barrier layer oxide of lower quality, and foil corrosion.

Various aspects of the present subject matter include performance properties which enable the capacitor to function as a single capacitor in an implantable cardioverter defibrillator 660. For example, by constructing the capacitor stack with the methods and apparatus contained in these teachings, one may construct a capacitor which is suited for use as the sole capacitor used for powering therapeutic pulses in an implantable cardioverter defibrillator. By using a single capacitor, instead of two capacitors which are connected in series, the present subject matter contributes to weight and size reductions.

Overall, the present subject matter offers multiple advantages. First, the present subject matter features capacitor designs which are compact and lightweight due to improved volumetric energy density. Smaller capacitors can enable smaller implantable medical devices, which tend to increase patient comfort. Additionally, increasingly effective capacitors can do the work of two less effective capacitors, reducing size and complexity of devices using capacitors. Reduced complexity can increase reliability and reduce manufacturing costs. Additional benefits, including those described elsewhere in this application, are within the scope of the present subject matter.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments, will be apparent to those of skill in the art upon reviewing the above description. The scope of the present subject matter should be determined with reference to the appended claims, along with the full scope of equivalents to which such claims are entitled.

What is claimed is:

1. A method, comprising:
   forming a first capacitor stack from at least a first element;
   forming a second capacitor stack from at least a second element;
   stacking the first capacitor stack onto the second capacitor stack into a capacitor electrode stack;
   welding a flexible bus to the first capacitor stack and the second capacitor stack;
   rotating the second capacitor stack away from the first capacitor stack and into a splayed position;
   positioning the first capacitor stack and the second capacitor stack in a case in the splayed position; and
   filling the case with electrolyte.

2. The method of claim 1, wherein the first element includes at least one first cathode, at least one first anode and at least one first separator in alignment.

3. The method of claim 1, wherein a first edge face of the first capacitor stack and a second edge face of the second capacitor stack are aligned in an unsplayed position and define a connection surface for connection of the flexible bus.

4. The method of claim 1, including welding the flexible bus to the case.

5. The method of claim 1, including:
   inserting the capacitor case into a device housing adapted for implant in a patient;
   connecting the capacitor to electronics in the device housing, the electronics connected to a connector passing from an interior of the housing to an exterior of the housing;
   sealing the device housing; and
   assembling the connector to a lead.

6. The method of claim 1, wherein the second capacitor stack is rotated approximately 180 degrees with respect to the first capacitor stack in the splayed position.

7. The method of claim 6, wherein the first capacitor stack and the second capacitor stack are similarly shaped, with the first capacitor stack defining a first long sidewall and a first short sidewall, and the second capacitor stack defining a second long sidewall and a second short sidewall, and the flexible bus connects the first long sidewall and the second long sidewall.

8. The method of claim 6, wherein the first capacitor stack and the second capacitor stack are similarly shaped, with the first capacitor stack defining a first long sidewall and a first short sidewall, and the second capacitor stack defining a second long sidewall and a second short sidewall, and the flexible bus connects the first short sidewall and the second short sidewall.

9. The method of claim 1, further comprising aging the first capacitor stack and the second capacitor stack.

10. The method of claim 1, wherein welding includes welding at least one flexible ribbon to a first capacitor electrode and a second capacitor electrode.

11. The method of claim 10, wherein rotating includes bending the flexible ribbon to divide the capacitor electrode stack and to splay the first element and the second element such that the first capacitor electrode is rotated with respect to the second capacitor electrode.

12. The method of claim 10, including welding the flexible ribbon to the case.

13. The method of claim 10, wherein a first edge face of the first element and a first edge face of the second element are aligned in an unsplayed position, and define a connection surface for connection of the flexible ribbon.

14. The method of claim 10, wherein the first element and the second element are similarly shaped.

15. The method of claim 14, wherein the first element defining a first long sidewall and a first short sidewall, and the second element defining a second long sidewall and a second short sidewall, and the flexible ribbon connects the first short sidewall and the second short sidewall.

16. The method of claim 14, wherein the first element defines a first long sidewall and a first short sidewall, and the second element defining a second long sidewall and a second short sidewall, and the flexible ribbon connects the first long sidewall and the second long sidewall.

17. The method of claim 1, wherein the second element includes at least one second cathode, at least one second anode and at least one second separator in alignment.

18. The method of claim 1, further comprising storing in the capacitor electrode stack from about 5.3 joules per cubic centimeter of capacitor stack volume of the capacitor electrode stack to about 6.3 joules per cubic centimeter of capacitor stack volume of the capacitor electrode stack at a voltage of between about 410 volts to about 610 volts.

19. The method of claim 15, further comprising storing in the capacitor electrode stack about 5.8 joules at a voltage of between about 410 volts to about 610 volts.

20. The method of claim 1, wherein rotating includes splaying the second capacitor stack away from the capacitor electrode stack and into a splayed position.

* * * * *